United States Patent [19]
Hess et al.

[11] Patent Number: 5,968,087
[45] Date of Patent: Oct. 19, 1999

[54] MULTI-COMPONENT LEAD BODY FOR MEDICAL ELECTRICAL LEADS

[75] Inventors: Douglas N. Hess, Maple Grove, Minn.; Stanton D. Myrum, Enchichens, Switzerland; Michael J. Ebert, Fridley, Minn.

[73] Assignee: Medtronic, Inc., Minneapolis, Minn.

[21] Appl. No.: 08/990,219

[22] Filed: Dec. 15, 1997

[51] Int. Cl.⁶ .................................................. A61N 1/05
[52] U.S. Cl. ........................ 607/127; 600/372; 607/122
[58] Field of Search .................... 600/372–376; 607/126, 127, 131; 604/524, 525

[56] References Cited

U.S. PATENT DOCUMENTS

| | | |
|---|---|---|
| 4,106,512 | 8/1978 | Bisping . |
| 4,135,518 | 1/1979 | Dutcher . |
| 4,355,646 | 10/1982 | Kallok et al. . |
| 4,840,186 | 6/1989 | Lekholm et al. . |
| 5,076,285 | 12/1991 | Hess et al. . |
| 5,246,014 | 9/1993 | Williams et al. . |
| 5,324,321 | 6/1994 | Pohndorf et al. . |
| 5,358,517 | 10/1994 | Pohndorf et al. . |
| 5,456,707 | 10/1995 | Giele . |
| 5,476,501 | 12/1995 | Stewart et al. . |

*Primary Examiner*—Linda G. M. Dvorak
*Assistant Examiner*—Roy Gibson
*Attorney, Agent, or Firm*—Reed A. Duthler; Harold R. Patton

[57] ABSTRACT

A medical electrical lead having an elongated lead body carrying a conductor therein, the lead body being formed of an inner sleeve of a first, relatively more rigid plastic and an outer sheath of a second, relatively less rigid plastic, the inner sleeve having a tubular portion and having outwardly extending helical ridges extending along its length, the ridges having lateral wall surfaces extending radially from the tubular portion and an outer sheath over the inner sleeve and in contact with the lateral wall surfaces of the inner sleeve. A fixation helix may be mounted at the distal end of the lead body and a conductor, which is also rotatable relative to the lead body may be located within the inner, tubular sleeve. Conductors may also be located between the ridges of the inner sleeve, embedded in the outer sheath.

9 Claims, 2 Drawing Sheets

MULTI-COMPONENT LEAD BODY FOR MEDICAL ELECTRICAL LEADS

BACKGROUND OF THE INVENTION

This invention relates generally to implantable medical electrical leads, and more particularly to implantable leads employing screw-in fixation mechanisms and to multi-conductor leads.

In implantable leads employing helical fixation members, twisting of the lead body due to applied torque makes implanting the lead more difficult for the physician. This is true whether the fixation mechanism is coupled mechanically to the lead body and rotated by rotation of the lead body itself, as in U.S. Pat. No. 5,076,285, issued to Hess et al. or the fixation mechanism rotated by means of a rotatable conductor located within the lead body as in U.S. Pat. No. 4,106,512, issued to Bisping. In the former case, twisting of the lead body due to torque applied at the proximal end results in the number of turns or rotations of the proximal end of the lead not corresponding to the number of turns of the distal end of the lead body carrying the helix. In the latter case, twisting of the lead body due to torque applied by the rotatable conductor along the length of the lead results in the number of turns or rotations of the proximal end of the rotatable conductor not corresponding to the number of turns or rotations of the helix relative to the distal end of the lead. In the context of leads employing rotatable fixation helixes, one approach to dealing with the problems due to the interaction of the rotatable conductor and the lead body has been to provide a slippery surface either on the conductor itself as in U.S. Pat. No. 5,456,707 issued to Giele or on the interior of the lead body as disclosed in U.S. Pat. No. 5,476,501 issued to Stewart et al.

In implantable leads employing multiple conductors, a wide array of configurations have been proposed, including co-axially arranged coils as in U.S. Pat. No. 4,355,646, issued to Kallok, conductors located in parallel lumens within the lead body, as in U.S. Pat. No. 4,135,518, issued to Dutcher and conductors embedded in the wall of the lead body, as in U.S. Pat. No. 4,840,186, issued to Lekholm et al. A two-piece lead body in which conductors are located between a ridged inner tubular member and an outer tubular member has been employed in implantable neurological leads and is disclosed in FIGS. 7 and 8 of Pending Provisional Application Serial No. 60/033,511, filed on Dec. 19, 1996 by Cross et al.

SUMMARY OF THE INVENTION

The present invention is directed toward a lead having a multi-component lead body which provides for improved transfer along the length of the lead and increased resistance to twisting due to torque applied to the lead body and further allows for production of a small diameter, multi-conductor lead. The present invention accomplishes these desired results by means of a two piece structure including an relatively thin inner sleeve molded of a first relatively more rigid plastic such as polyethylene, polyurethane, PTFE, Kynar or the like, which is provided with an outwardly extending helical ribs or ridges, covered by an outer sheath of a second, relatively less rigid but highly biocompatible plastic such as silicone rubber. In the context of a lead employing a helical fixation device, the plastic employed for the inner sleeve is chosen to display a low coefficient of friction. The outer sheath is molded or extruded over the inner sleeve so that it is in contact with the radially extending lateral wall surfaces of the inner sleeve. Interaction of the helical ribs or ridges with the outer sheath of the lead body provides for a highly efficient transfer torque along the length of the lead, while the lubricious nature of the plastic chosen for the inner sleeve provides for the additional benefit of a reduction of frictional engagement between the rotatable coil conductor coupled to the fixation helix and the lead body, in turn reducing the amount of torque applied to the lead body by the conductor coil. In the context of a lead employing a screw mounted fixedly to the lead body, the two component lead body construction of the present invention enhances the ability to transfer torque via the lead body to the fixation helix.

In the context of multi-conductor implantable leads generally, the composite lead body structure has an additional benefit in that conductors for coupling to electrodes, sensors, or other electronic components carried by the lead may conveniently be located between adjacent ones of the ribs or ridges, and thereafter enclosed by the outer sheath of the lead body. In this fashion, multiple lead conductors may be arranged around the periphery of the body without the necessity of insulating individual ones of the conductors from one another and without the necessity of increasing the diameter of the lead body with increases in the number of conductors. In addition, by varying the pitch of the helical ridges or ribs, their number and/or their cross-sectional configuration, the mechanical characteristics of the lead body may be optimized and may be varied along the length of the lead to provide a wide variety of desired mechanical characteristics while maintaining a uniform outer diameter.

DETAILED DESCRIPTION OF THE PREFERRED EMBODIMENTS

Figure 1:
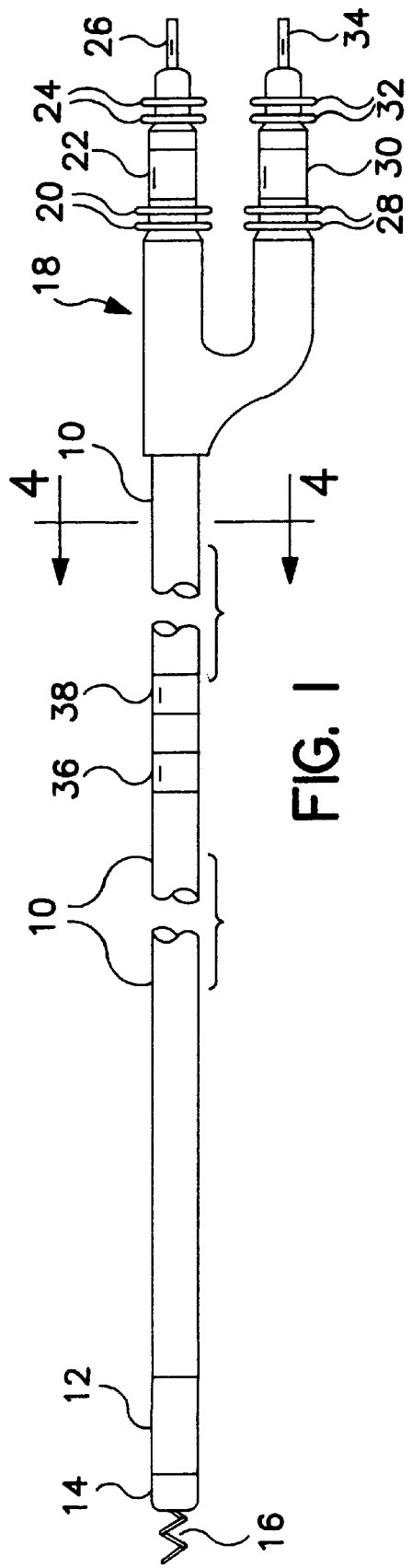
FIG. 1 is a plan view of a lead employing the present invention.

FIG. 1 is a plan view of a lead according to the present invention. The lead is provided with an elongated lead body 10 which carries an electrode head 12 at its distal extremity from which a rotatable helical electrode 16 extends. Helical electrode 16 serves to sense and pace in the ventricle of a patient's heart and also to affix the distal end of the lead to heart tissue. End cap 14 is mounted at the distal end electrode head 12 and in the embodiment serves to retain a monolithic controlled release device (MCRD) which dispenses an anti-inflammatory steroid drug such as sodium dexamethazone phosphate.

Ring electrodes 36 and 38 are located along the lead body in a location chosen such that when helical electrode 16 is engaged with tissue in the right ventricular apex of a human heart, ring electrodes 36 and 38 are located in the right atrium of the heart, where they may be employed to sense atrial depolarizations. At the proximal end of the lead is a bifurcated connector assembly 18 which carries on its first arm connector pin 26 and connector ring 22, as well as sealing rings 20 and 24. Connector pin 26 is coupled to helical electrode 16 by means of an elongated coiled conductor running the length of the lead. In the fashion disclosed in U.S. Pat. No. 4,106,512 issued to Bisping and incorporated by reference in its entirety, rotation of connector pin 26 causes rotation of helical electrode 16 and advancement of helical electrode 16 out the distal end of electrode head 12. Connector ring 22 is not electrically coupled to any other components of the lead in the illustrated embodiment, however, connector ring 22 in alternative embodiments might be coupled to an additional electrode or a physiologic sensor such as a pressure transducer, oxygen sensor, temperature sensor or the like. On the second arm of connector assembly 18 are connector pin 34, connector ring 30 and sealing rings 28 and 32. Connector pin 34 is coupled to ring electrode 36 while connector ring 30 is coupled to connector ring 38.

Figure 2:
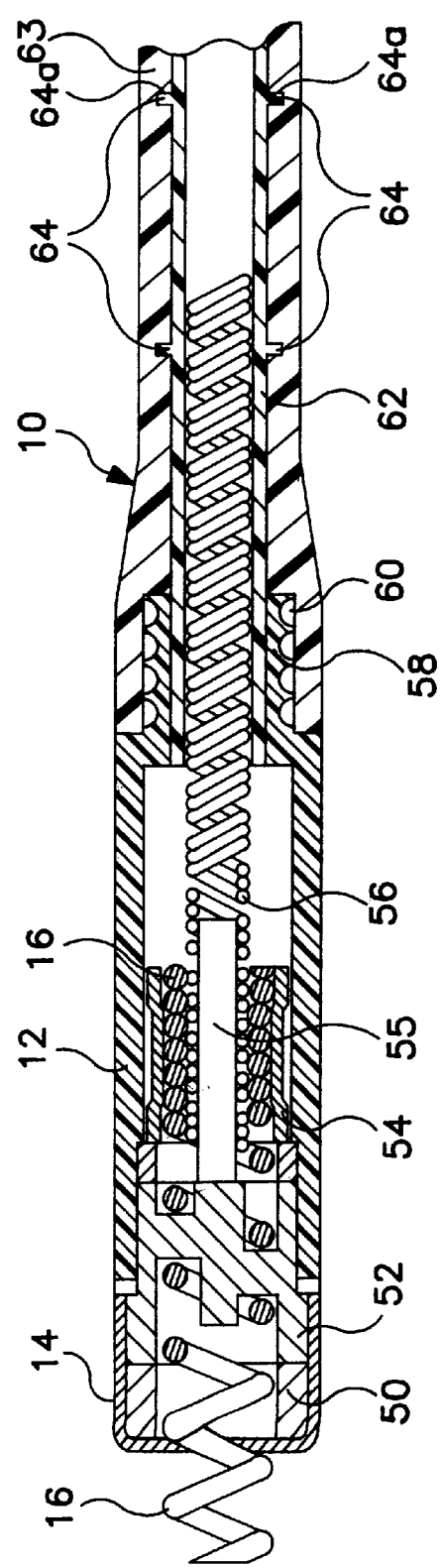
FIG. 2 is a cross-sectional view through the distal portion of a lead employing the present invention.

FIG. 2 is a cross-section through the distal portion of the lead illustrated in FIG. 1. In this view, it is apparent that electrode head 12 is provided with an internal lumen in which helical electrode 16 is rotatably located. Movement of helical electrode 16 is controlled by guide member 52. When helical electrode 16 is rotated relative to guide member 52, it is advanced or retracted from the distal end of electrode head 12, depending upon the direction of rotation. The proximal end of helical electrode 16 is coupled to coiled conductor 56 by means of crimping sleeve 54 and crimping core 55, so that rotation of conductor 56 causes rotation of helix 16 and its corresponding advancement or retraction from electrode head 12. Lead body 10 is visible in cross-section and comprises two components, including a first inner sleeve 62 which takes the form of a tube of a relatively more rigid or stiffer plastic such as polyurethane, polyethylene, PTFE, Kynar or other plastic having a relatively low coefficient of friction with respect to helical conductor 56. Inner sleeve 62 is provided with one or more helical ridges or ribs 64 which extend along the length of inner sleeve 62. The second component of lead body 10 is the outer sheath 63 which encloses and surrounds inner sleeve 62. Outer sheath or sleeve 63 is formed of a second relatively softer or less rigid plastic, for example silicone rubber, which is extremely biocompatible and stable within the human body. The provision of helical ribs or ridges 64 on inner sleeve 62 provides for an enhanced ability of the lead body to transmit torque along its length and to resist twisting due to applied torque. Because the outer sheath is molded or extruded over the inner sleeve, the outer sheath is in contact with the radially extending lateral wall surfaces 64a, providing a composite structure of high torsional rigidity while retaining most of the flexibility associated with the material of the outer sheath 63. The choice of a plastic for inner sleeve 62 having a relatively low coefficient of friction with respect to coiled conductor 56 also reduces the amount of torque applied to lead body 10 by rotation of conductor 56. Lead body 10 is coupled to the proximal end of electrode head 12 by means of adhesive 60 which is located within the grooves of threaded portion 58 of electrode head 12.

Figure 3:
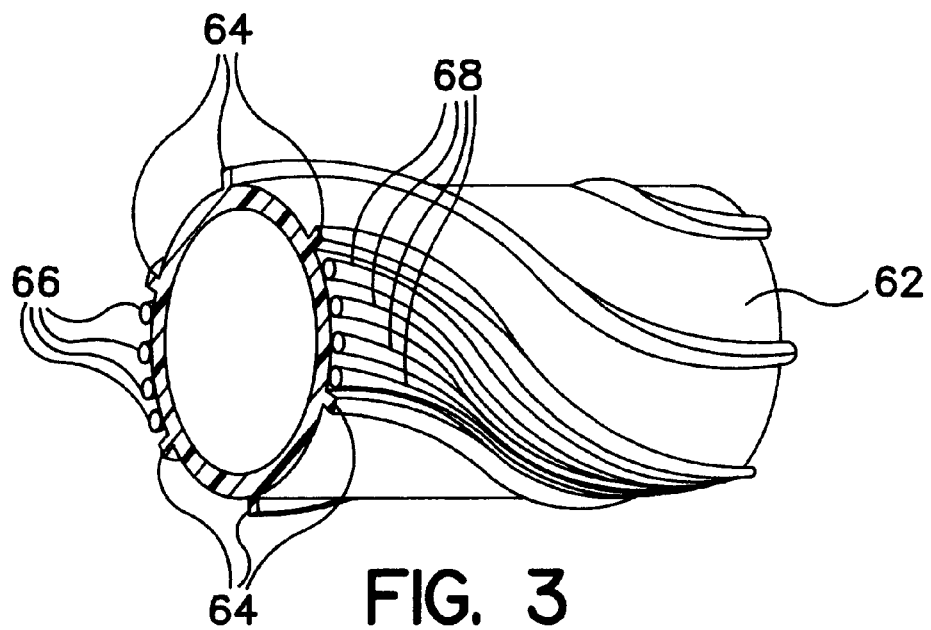
FIG. 3 is a perspective view of a portion of the inner sleeve of a lead body according to the present invention, carrying conductors between the spiral ribs or ridges of the inner sleeve.

FIG. 3 illustrates a configuration of inner sleeve 62, and associated ribs or ridges 64. In this view it can be seen that ribs or ridges 64 are wound helically around inner sleeve 62. Although not illustrated in FIG. 3, the pitch at which ridges or ribs 64 are wound around inner sleeve 62 may vary along the length of the lead to provide greater or lesser amounts of torsional rigidity along the length of the lead body without varying the lead body diameter. Also illustrated are two sets of conductors 66 and 68 located between adjacent ones of the ridges 64. One set of conductor 66 may, for example, be coupled to electrode 36 (FIG. 1) and connector pin 24 while the second set of conductors 68 may, for example, be coupled to electrode 38 and connector ring 30. Conductors 66 and 68 may be, for example, stranded conductors as in U.S. Pat. No. 5,246,014, issued to Williams et al, or solid conductors as disclosed in U.S. Pat. No. 5,358,517, issued to Pohndorf et al., or U.S. Pat. No. 5,324,321, issued to Pohndorf et al., all incorporated herein by reference in their entireties or may be any other appropriate conductor used in electrical leads. Different numbers of conductors may be located intermediate adjacent ridges or ribs, and greater or fewer numbers of the spaces between adjacent ridges or ribs may be employed to locate electrical conductors. In this way, the basic two-component lead body configuration of the present invention may usefully be applied to a wide variety of electrical lead types, with variable numbers and spacings of electrodes, sensors or other electrical components located along the lead without having to increase the diameter of the lead body to accommodate additional conductors. In addition, the pitch or cross sectional configuration of the ribs or ridges may be varied along different portions of the lead body depending on the number of conductors extending along the particular portions so that the to provide relatively uniform mechanical properties along the length of the lead if so desired. The same considerations allow the production of families of leads having different numbers of conductors but relatively uniform mechanical properties.

Figure 4:
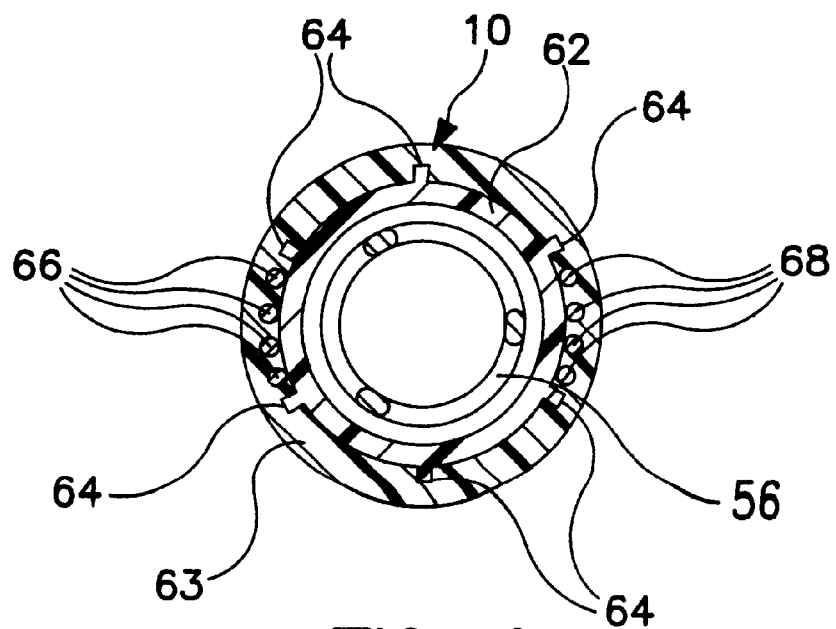
FIG. 4 is a cross-sectional view through the proximal portion of the lead body of the lead illustrated in FIG. 1.

FIG. 4 is a cross-sectional view through the lead of FIG. 1 in a proximal portion of the lead body. Coiled conductor 56 is seen located within inner sleeve 62. Conductors 66 and 68 are seen located between adjacent ones of ribs or ridges 64 extending from inner sleeve 62. Outer sheath 63 is shown surrounding and enclosing conductors 66 and 68 and inner sleeve 62. Outer sheath 63 may be applied to the assembly of conductors 66 and 68 and inner sleeve 62 by means of extrusion, molding, or the like and completely encloses conductors 66 and 68. Conductors 66 and 68 may terminate along the length of the lead, with their ends brought out through outer sheath 63 and welded, crimped, swaged or otherwise coupled to ring electrodes 36 and 38. Alternatively, conductors 66 and 68 may simply continue along the entire length of the lead, contributing to its torsional rigidity, with portions of outer sheath 63 removed in areas in which the conductors are to be coupled to ring electrodes 36 and 38.

While the above illustrated embodiment of the lead according to the present invention is a cardiac pacing lead with an extendible fixation helix, the structure of the lead body is also believed especially suited for use in conjunction with leads employing fixation helixes which are not rotatable with regard to the lead body, as discussed above. In addition, certain aspects of the two-component lead body construction in the present invention are believed useful in the context of medical electrical leads employing a number of conductors coupled to multiple, mutually insulated electrical components generally, including leads which do not employ fixation helixes. As such, the above disclosed embodiment should be considered exemplary, rather than limiting, with regard to the claims which follow.

In conjunction with the above disclosure, we claim:

1. A medical electrical lead, comprising:
an elongated lead body having proximal and distal ends;
a fixation helix mounted at the distal end of the lead body; and
a conductor extending along the lead body; and
wherein the lead body comprises an inner sleeve of a first, relatively more rigid plastic and an outer sheath of a second, relatively less rigid plastic, the inner sleeve having a tubular portion and having outwardly extending helical ridges extending along its length, the helical ridges having lateral wall surfaces extending radially from the tubular portion and an outer sheath over the inner sleeve and in contact with the lateral wall surfaces of the inner sleeve.

2. A lead according to claim 1 wherein the helix is rotatable relative to the lead body and is coupled to the conductor, which is also rotatable relative to the lead body and is located within the inner, tubular sleeve.

3. A medical electrical lead, comprising:

an elongated lead body having proximal and distal ends; and multiple conductors extending along the lead body; and wherein the lead body comprises an inner, tubular sleeve of a first, relatively more rigid plastic and an outer sheath of a second, relatively less rigid plastic, the inner sleeve having a tubular portion and having outwardly extending helical ridges extending along its length, the ridges having lateral wall surfaces extending radially from the tubular portion and an outer sheath over the inner sleeve and in contact with the lateral wall surfaces of the inner sleeve, the conductors located between adjacent ones of the helical ridges.

4. A lead according to claim 1 or claim 3 wherein the helical ridges of said inner sleeve vary in pitch along the sleeves length.

5. A lead according to claim 1 or claim 3 wherein said lead comprises a conductor embedded in the outer sheath, located between adjacent ones of the helical ridges of the sleeve.

6. A medical electrical lead, comprising:

an elongated lead body having proximal and distal ends;

a fixation helix mounted at the distal end of the lead body; and a conductor extending along the lead body; and wherein the lead body comprises an inner, sleeve of a first, relatively more rigid plastic and an outer sheath of a second, relatively less rigid plastic, the inner sleeve having a tubular portion and having outwardly extending ridges extending along its length, the ridges having lateral wall surfaces extending radially from the tubular portion and an outer sheath over the inner sleeve and in contact with the lateral wall surfaces of the inner sleeve.

7. A lead according to claim 6 wherein the helix is rotatable relative to the lead body and is coupled to the conductor, which is also rotatable relative to the lead body and is located within the inner, tubular sleeve.

8. A medical electrical lead, comprising:

an elongated lead body having proximal and distal ends; and multiple conductors extending along the lead body; and wherein the lead body comprises an inner, tubular sleeve of a first, relatively more rigid plastic and an outer sheath of a second, relatively less rigid plastic, the inner sleeve having a tubular portion and having outwardly extending ridges extending along its length, the ridges having lateral wall surfaces extending radially from the tubular portion and an outer sheath over the inner sleeve and in contact with the lateral wall surfaces of the inner sleeve, the conductors located between adjacent ones of the ridges.

9. A lead according to claim 6 or claim 8 wherein said lead comprises a conductor embedded in the outer sheath, located between adjacent ones of the ridges of the sleeve.

* * * * *